US006940945B2

(12) United States Patent
  Maschke

(10) Patent No.: US 6,940,945 B2
(45) Date of Patent: Sep. 6, 2005

(54) METHOD FOR PRODUCING AN X-RAY IMAGE

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 83 days.

(21) Appl. No.: 10/681,596

(22) Filed: Oct. 8, 2003

(65) Prior Publication Data

US 2004/0071265 A1 Apr. 15, 2004

(30) Foreign Application Priority Data

Oct. 8, 2002 (DE) .......................................... 102 46 904

(51) Int. Cl.[7] .............................................. H05G 1/64
(52) U.S. Cl. .................................................. 378/98.12
(58) Field of Search ................................ 378/65, 98.12

(56) References Cited

U.S. PATENT DOCUMENTS

| | | | | |
|---|---|---|---|---|
| 4,943,987 A | * | 7/1990 | Asahina et al. | ............ 378/98.5 |
| 5,594,771 A | * | 1/1997 | Kawai | ........................ 378/98.2 |
| 5,852,646 A | | 12/1998 | Klotz et al. | |
| 6,256,368 B1 | * | 7/2001 | Hsieh et al. | .................... 378/8 |

* cited by examiner

*Primary Examiner*—Craig E. Church
*Assistant Examiner*—Thomas R. Artman
(74) *Attorney, Agent, or Firm*—Schiff Hardin LLP

(57) ABSTRACT

In a method for producing an x-ray image, during two time-separated examination dates, a first x-ray image and a second x-ray image of a body region of an organism are respectively generated. The x-ray image datasets associated with the two x-ray images are subtracted from one another, so that a further image dataset ensues. Subsequently, the image information of the image dataset is emphasized and superimposed with the image information of the second x-ray image dataset.

4 Claims, 2 Drawing Sheets

METHOD FOR PRODUCING AN X-RAY IMAGE

BACKGROUND OF THE INVENTION

1. Field of the Invention

The present invention concerns a method for producing an x-ray image.

2. Description of the Prior Art

The course of a tumor or carcinoma treatment of a patient is, among other things, monitored by making x-ray exposures at temporal intervals of the body region of the patient that is affected by the tumor or the carcinomas. A physician then compares the exposures to each other. Due to changes visible in the x-ray images, the physician can make conclusions about the course of the tumor or carcinoma treatment.

SUMMARY OF THE INVENTION

An object of the present invention is to provide a method with which changes that are visible in two x-ray images that are made of a body region of a patient at two different examination dates can be more easily recognized.

This object of the invention is achieved in a method for producing an x-ray image, including the steps of producing of an image dataset in which the image information if a first x-ray image dataset is subtracted from the image information of a second x-ray image dataset, a first x-ray image of an organism being associated with the first x-ray image dataset and a second x-ray image of an organism being associated with the second x-ray image dataset, the first x-ray image dataset and the second x-ray image dataset being respectively produced during two difficult examination dates, and the first x-ray image and the second x-ray image are substantially associated with the same projection emphasizing of the image information of the image dataset, and superimposing the image information of the image dataset on the image information of the second x-ray image dataset.

X-ray image datasets associated with both of the x-ray images of the organism are subtracted from one another. The x-ray images associated with both x-ray image datasets are generated from the same body region of the organism with substantially the same projections, and during two different examination dates. Between the two examination dates is a time span, for example a number of months. Due to the subtraction of both x-ray image datasets, the resulting image dataset shows how the body region of which the x-ray exposure was made has changed between the two examination dates. If the image dataset is used, for example, to monitor a tumor or carcinoma treatment, the resulting image dataset shows in particular a change of the tumor or carcinoma. The image information of the resulting image dataset is subsequently emphasized and superimposed with the image information of the second x-ray image dataset. The image information of the resulting image dataset is in particular superimposed with the image information of the second x-ray image dataset, by adding or subtracting the image information of the second x-ray image dataset. The x-ray image that thereby ensue can then be viewed, for example with a finding monitor. Due to the emphasized image information of the image dataset that reproduces the changes between both examination dates, the changes are likewise emphasized in the x-ray image displayed on the finding monitor. A doctor can thus recognize the changes in a relatively simple manner, whereby his or her work is facilitated and he or she is less likely to overlook a change.

In preferred embodiments of the invention, the image information of the image dataset is emphasized or intensified in color.

Since in hospitals and radiology practices, x-ray images of the thorax are frequently produced in a version of the invention, the body region is the thorax of the organism.

DESCRIPTION OF THE PREFERRED EMBODIMENTS

Figure 1:
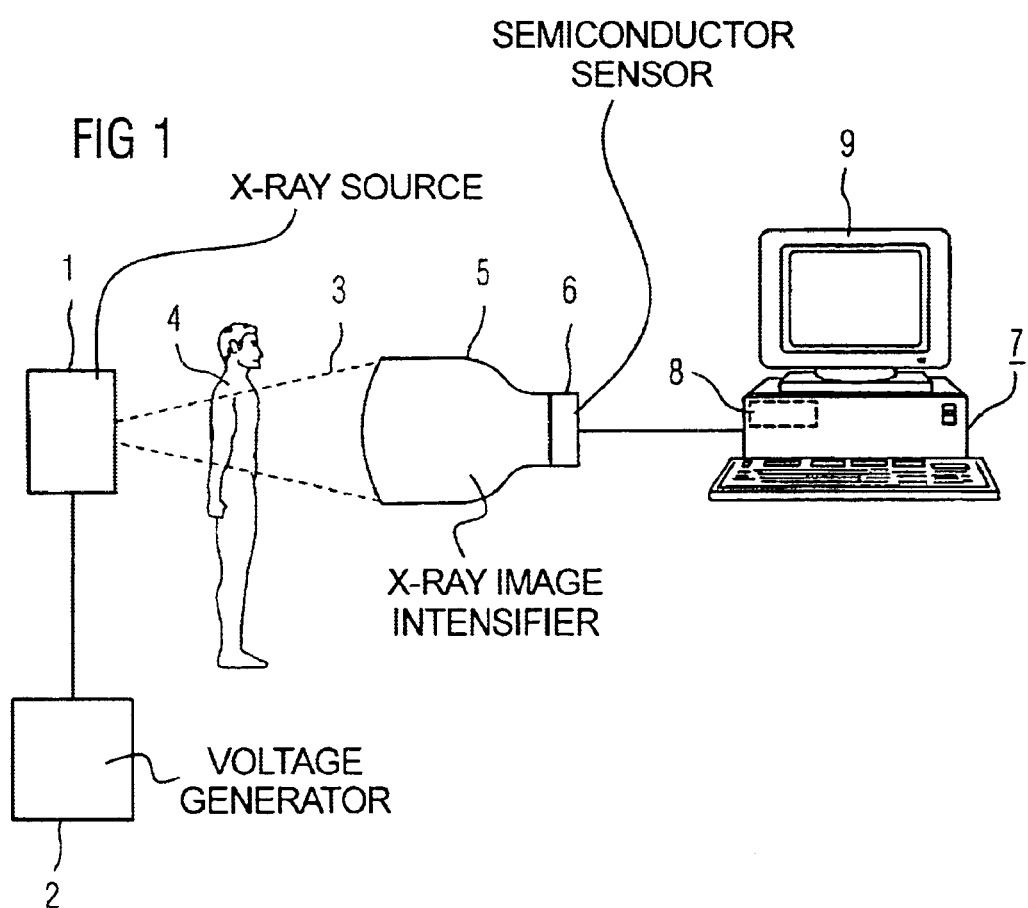
FIG. 1 schematically illustrates an x-ray diagnostic device operable in accordance with the invention.

The x-ray diagnostic device shown partially as a block diagram in FIG. 1 has an x-ray source 1 operated by a voltage generator 2. The x-ray source 1 in operation emits an x-ray beam 3 having edge rays shown dashed in FIG. 1. The x-ray beam permeates a patient 4 and strikes an x-ray image intensifier 5 as an x-ray image, attenuated corresponding to the transparency of the patient 5. A semiconductor sensor 6, with corresponding electronics that transduce the output signal of the x-ray image intensifier 5 into electronic signals, is connected following the x-ray image intensifier 5, such that an x-ray image dataset ensues from each x-ray image from the x-ray image intensifier 5.

The x-ray image datasets, corresponding in the exemplary embodiment to the DICOM standard that is typical in medical technology, are stored on a hard drive 8 associated with a computer 7 connected with the x-ray diagnostic device. Since the x-ray image datasets in the exemplary embodiment exist in the DICOM standard, information is stored in a header associated with the x-ray image dataset, such as for example the image dimensions, the number of pixels, the pixel size, and the scaling factor of the x-ray image associated with the corresponding x-ray image dataset.

Moreover, the x-ray images associated with the x-ray image datasets stored on the hard drive 8 of the computer 7 can be viewed with a monitor 9 that is connected to the computer 7.

Figure 2:
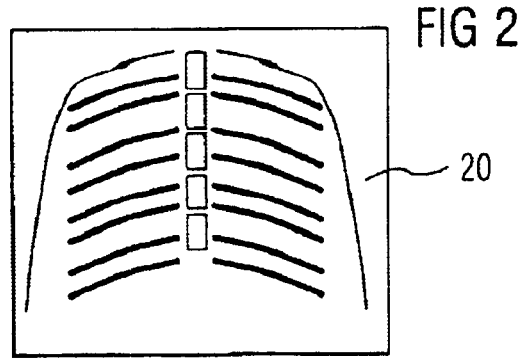
FIGS. 2 through 5 show respective x-ray images for explaining the invention.

In the exemplary embodiment, a computer program is stored on the computer 7 with which an image dataset can be generated based on a subtraction of two x-ray image datasets stored on the hard drive 8. The x-ray image datasets used for the image dataset are generated on two different examination dates and are of the same body region of a patient. Moreover, the x-ray images associated with the x-ray image datasets are acquired in the same projection. In the exemplary embodiment, the corresponding x-ray images are x-ray images of the thorax of the patient 4. One of the images was acquired at an earlier examination date. It is shown as an example in FIG. 2 and provided with reference number 20. The second x-ray image was acquired at a later examination date, such as during the current examination of the patient 4. It is shown as an example in FIG. 3 and provided with reference number 30. In the exemplary embodiment, approximately six months exist between the examination dates.

Due to the information stored in the headers respectively associated with the x-ray image datasets about the image dimensions, the number of pixels, pixel sizes, and the scaling factors, it is possible to superimpose the image data of both x-ray image datasets true to scale and then to subtract them from one another, similar to digital subtraction angiography (DSA). The superimposition true to scale is, in the present exemplary embodiment, achieved by (among other things) pixel shifting, a method known from angiography. The methods for pattern recognition known to those skilled in the art also are used. In the case of x-ray images of the thorax, the contours of the ribs can be recognized, and by means of this information the x-ray image datasets can be superimposed accurate to size.

Figure 3:
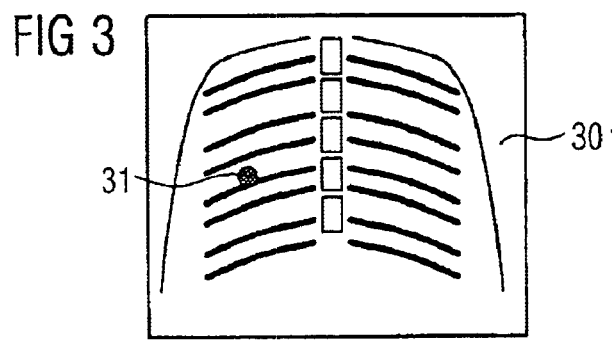

In the exemplary embodiment, the x-ray image dataset acquired at the earlier examination date (that is associated with the x-ray image 20 shown in FIG. 2) is subtracted from the x-ray image dataset acquired at the later examination date (the appertaining x-ray image 30 of which is shown in FIG. 3). The image associated with the resulting image dataset is shown in FIG. 4 and provided with the reference number 40.

Figure 4:
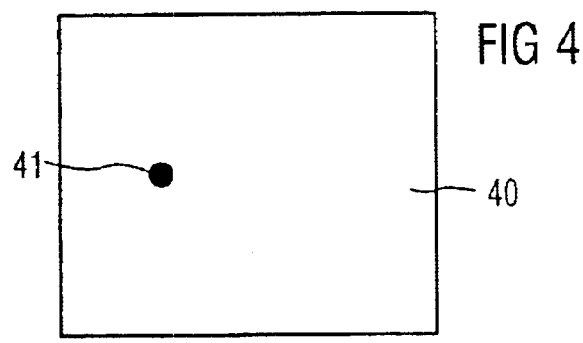

Due to the subtraction, the image 40 shown in FIG. 4 exhibits the difference between the two x-ray images 20 and 30. In order to highlight the difference, in the exemplary embodiment it is provided to emphasize with color the image points (pixels) of the resulting image dataset and emphasized with color. An intensification of the image data is also suitable for emphasis of the image information of the image dataset. In the exemplary embodiment, an image 31 of a tumor is visible in the x-ray image 30 that is not present in the x-ray image 20. The image 31 of the tumor is thus the difference between the two x-ray images 20 and 30. The image of the tumor is emphasized in the image 40 and provided with the reference number 41.

Figure 5:
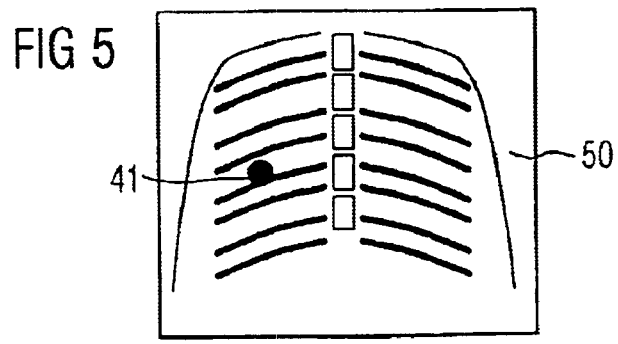

Subsequently, the image dataset and x-ray image dataset (that was acquired at the later examination date and that is associated with the x-ray image 30 shown in FIG. 3) are added. The x-ray image 50 associated with this x-ray image dataset is shown in FIG. 5. In the resulting x-ray image 50, the emphasized image 40 of the tumor is consequently emphasized in color.

In the exemplary embodiment, x-ray images 20 and 30 of the thorax of the patient 4 are used. In principle, the inventive method is also applicable for x-ray images of the same organ or other body regions. Similar to the method of harmonization (Dynamic Density Optimization), before the subtraction the x-ray image datasets can be scaled with an adjustable subtraction factor. The image dataset can also be provided with an adjustable factor before the addition with the corresponding x-ray image dataset.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for producing an x-ray image, comprising the steps of:

at respective time-separated times, generating a first x-ray image dataset containing image information of a body region of a subject and generating a second x-ray image dataset containing image information of substantially the same body region, at a same projection for each of said first and second x-ray image datasets;

subtracting the image information in one of said first and second x-ray image datasets from the image information in the other of said first and second x-ray image datasets to produce a subtraction image dataset containing image information;

emphasizing the image information in said subtracted image dataset to obtain emphasized image information; and superimposing the emphasized image information of said subtraction image dataset on said image information of said second x-ray image dataset.

2. A method as claimed in claim 1 comprising emphasizing the image information of said subtraction image dataset in color.

3. A method as claimed in claim 1 comprising emphasizing said image information of said subtraction image dataset by intensification.

4. A method as claimed in claim 1 comprising selecting a thorax of a living subject as said body region.

* * * * *